United States Patent [19]
Genova

[11] Patent Number: 5,590,650
[45] Date of Patent: Jan. 7, 1997

[54] NON-INVASIVE MEDICAL MONITOR SYSTEM

[75] Inventor: James J. Genova, Alexandria, Va.

[73] Assignee: Raven, Inc., Alexandria, Va.

[21] Appl. No.: 345,065

[22] Filed: Nov. 16, 1994

[51] Int. Cl.$^6$ ........................................... A61B 5/00
[52] U.S. Cl. ................. 128/630; 128/633; 128/653.001; 128/660.003; 128/664; 128/665; 128/668; 128/721; 128/670; 128/736; 128/748
[58] Field of Search .................................. 128/670, 671, 128/721, 722, 774, 782, 630, 664–6, 660.02, 660.03, 696, 658.01, 736, 748, 633, 668

[56] References Cited

U.S. PATENT DOCUMENTS

| | | | |
|---|---|---|---|
| 5,002,060 | 3/1991 | Nedivi | 128/671 |
| 5,105,354 | 4/1992 | Nishimura | 128/671 |
| 5,143,078 | 9/1992 | Mather et al. | 128/671 |
| 5,448,996 | 9/1995 | Bellin et al. | 128/671 |

Primary Examiner—Angela D. Sykes
Assistant Examiner—Robert L. Nasser, Jr.
Attorney, Agent, or Firm—David Fink

[57] ABSTRACT

An apparatus operable for monitoring physiological vital signs of a human body without physically contacting the body is disclosed. The apparatus includes a sensor operable to transform a movement and/or acoustical wave produced by the body into an electrical signal, a signal processor coupled to the sensor and operable to receive the electrical signal from the sensor and to process the electrical signal adaptively using wavelet correlator analysis. The signal processor provides an output signal indicative of the movement and/or acoustical wave producing the electrical signal. Typically, the apparatus can be used to monitor heart rate, respiration rate and related sounds, digestive system sounds as well as other physiological vital signs considered both essential and desirable for the evaluation of the health of a person.

8 Claims, 8 Drawing Sheets

NON-INVASIVE MEDICAL MONITOR SYSTEM

TECHNICAL FIELD

The present invention relates to a system and process for the monitoring of physiological vital life signs, and particularly to a non-invasive system and process.

Background of the Invention

It is well known that the initial encounter with a physician involves the physician evaluating various physiological vital signs such as heart rate, heart sounds, respiration rate, respiration sounds, blood flow, digestive processes and other parameters which can create acoustical movement and/or vibrations. This information is even taken when a person is reasonably well for later use as a frame of reference because these physiological vital signs are regarded as a general measure of the state of a person's health.

During treatment in a hospital, these physiological vital signs are monitored closely, particularly if a patient is severely sick or the status of the patient such as an infant may be critical. Thus, the collection of information relating to physiological vital signs is regarded as essential for competent medical care.

Typically, physiological vital signs are collected through the use of devices in direct contact with a person's body. It is well known that the acoustical information is very weak, that is, it has a very low signal to noise value so that direct contact of the pickup device is used to minimize external noise and to have the pickup device close to the source of the acoustical vibrations. Some medical information requires many direct contacts to the skin such as ECG systems. Very weak sounds require highly specialized equipment designed for a specific task of collecting a limited class of data.

The acquisition of the physiological vital signs from the many patients in a hospital is time consuming and is an inefficient use of talented personnel. Even if the data being collected is minimal, the effort remains significant because the medical specialist must encounter each patient personally and physically contact the patient with an instrument. In addition, the use of a direct contact pickup on patients is uncomfortable for many patients, especially if the patent is very sick and requires frequent monitoring. The difficulty in using a device attached to a patient for monitoring physiological vital signs is compounded not only by the movement of the patient in the bed but by a patient who wants to move from a bed to a chair, or to a wheelchair, or to another location.

Accordingly, it is seen that a need exists for a simple and effective system and method to monitor physiological vital signs. There is also a need for a non-invasive system which allows the movement of patients from a bed to some other place without terminating the monitoring activities. Furthermore, there is a need for a system which is adaptable to a variety of situations such as chairs, beds, wheelchairs, etc. and is relatively inexpensive.

SUMMARY OF THE INVENTION

The present invention overcomes the disadvantages of the prior art by providing a monitor which allows the monitoring of manifold physiological vital signs and is adaptable to a wide variety of settings including chairs, beds, wheelchairs, and other environments. The invention also provides a non-invasive monitor which adapts to be responsive to a patient's particular vital signs being monitored.

The present invention in one embodiment enables the monitoring of physiological vital signs without contacting the subject. The invention includes a sensing means operable to transform movements and/or acoustical waves into an electrical signal, signal processing means coupled to the sensing means and operable to receive the electrical signal from the sensing means and to process the electrical signal adaptively using wavelet correlator analysis techniques. The signal processing means has an output indicative of the movement and/or acoustical wave producing the electrical signal.

As used herein, a "wave correlator analysis" is a coherent matched filtering performed in real time between the conditioned data and the range of wavelets from the 'master wavelet filtering' as described herein.

DETAILED DESCRIPTION OF THE PREFERRED EMBODIMENTS

General Description

Figure 1:
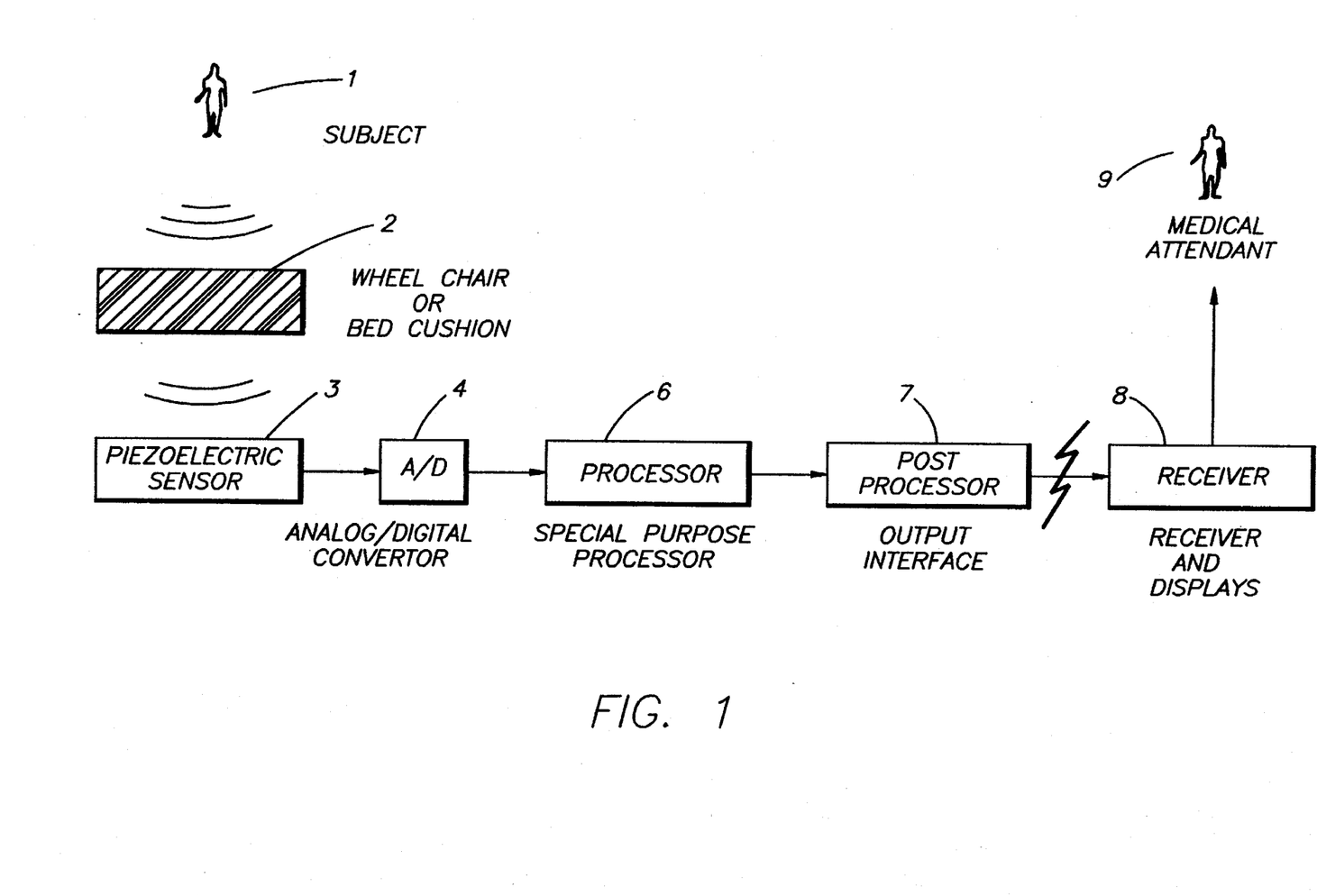
FIG. 1 is a block diagram showing a system according to the invention.

FIG. 1 shows an overall view of one embodiment of the invention being used to monitor the physiological vital signs of a subject 1. The subject 1 is positioned in a wheelchair or bed not shown and resting on cushion 2. Sensors such as piezoelectric sensors 3, or fiber optic pressure or motion sensors, or air or liquid diaphragm or the like are used to transform acoustical waves or motion into an electrical signal. Suitable devices are available commercially and need not be highly sensitive because the invention enables the detection and analysis of physiological vital signs represented by weak electrical signals with relatively poor signal to noise.

Thus, one of the advantages of the invention is that relatively inexpensive sensors can be used, thereby avoiding large expenses to equip numerous chairs, beds, wheelchairs and the like with sensors so that the subject is not only free to move in bed, but can move from bed to chair or any convenient place without concern of contact devices.

The electrical signal from the piezoelectric sensor 3 is coupled to an analog to digital converter 4 which has an output signal coupled to a processor 6 according to the invention. The output signal from the processor 6 is coupled to a post processor 7 which provides an interface between the processor 6 and device being used for communicating the information from processor 6 to another device or person. The embodiment shown in FIG. 1 communicates the output signal of the post processor 7 to a receiver 8 which displays the information for use by a medical attendant 9. The output signal of the post processor 7 can be hardwired or can transmit the information to a remote location such as a nurse's station.

Figure 2:
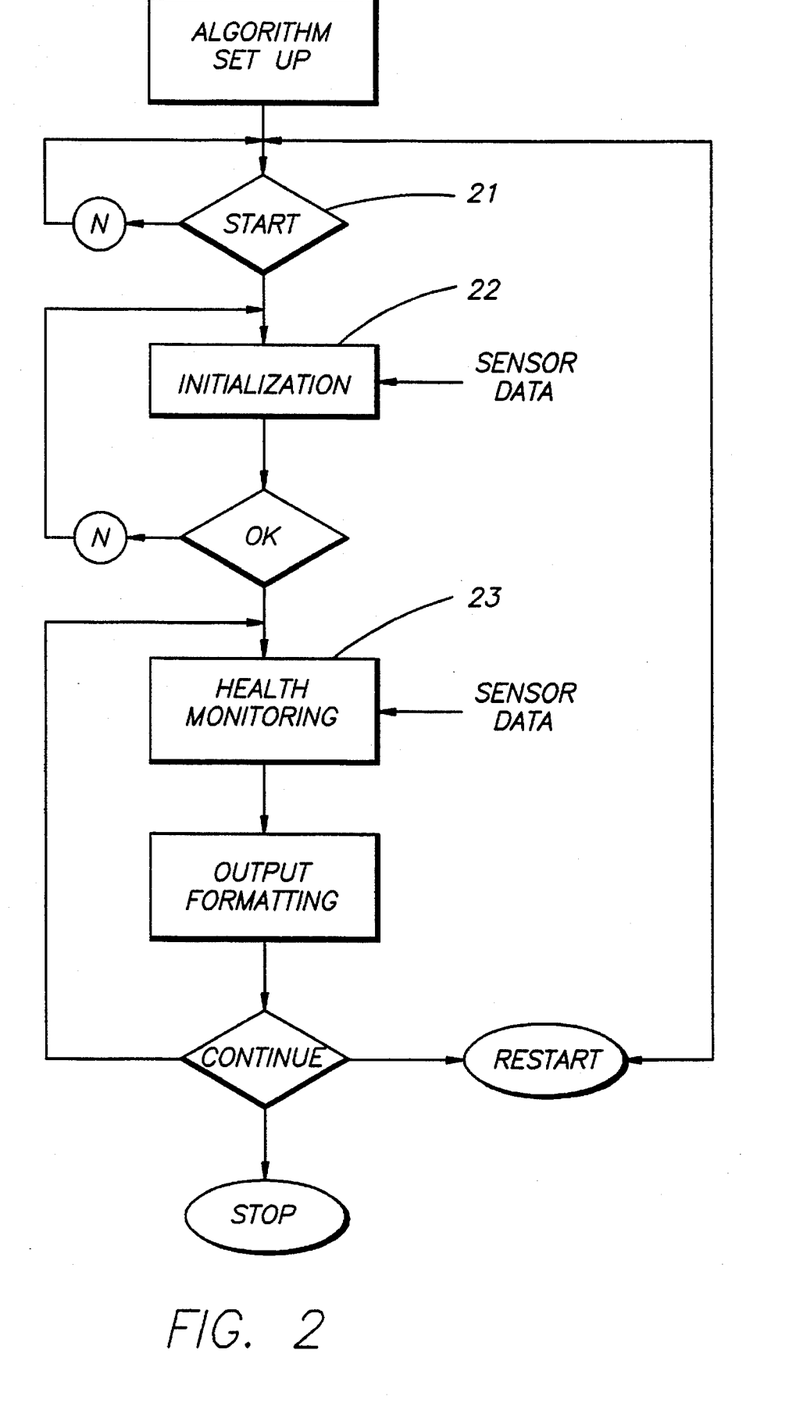
FIG. 2 is a flow diagram showing the main elements used in carrying out the invention shown in FIG. 1.

FIG. 2 shows the main functional elements of the algorithm used in the processor of the invention. The following is a general description of the operation. Typically, the medical attendant indicates at block 20 that there is a new patient to be monitored or analyzed and the start is indicated in block 21. The initialization sequence in block 22 has signals from sensors not shown and establishes matched filters or wavelets corresponding to selected parameters such as the last heart beat and the heart rate. The initialization can take several seconds, typically less than 5 seconds. During the initialization, a built in test is performed to instruct the algorithm to repeat or continue to the next stage. The sensors also provide data to the health monitoring block 23. The output signals from the block 23 are formatted and transmitted as required and various interrupts are serviced. More details of the operation will be provided in connection with other Figures herein.

Figure 3:
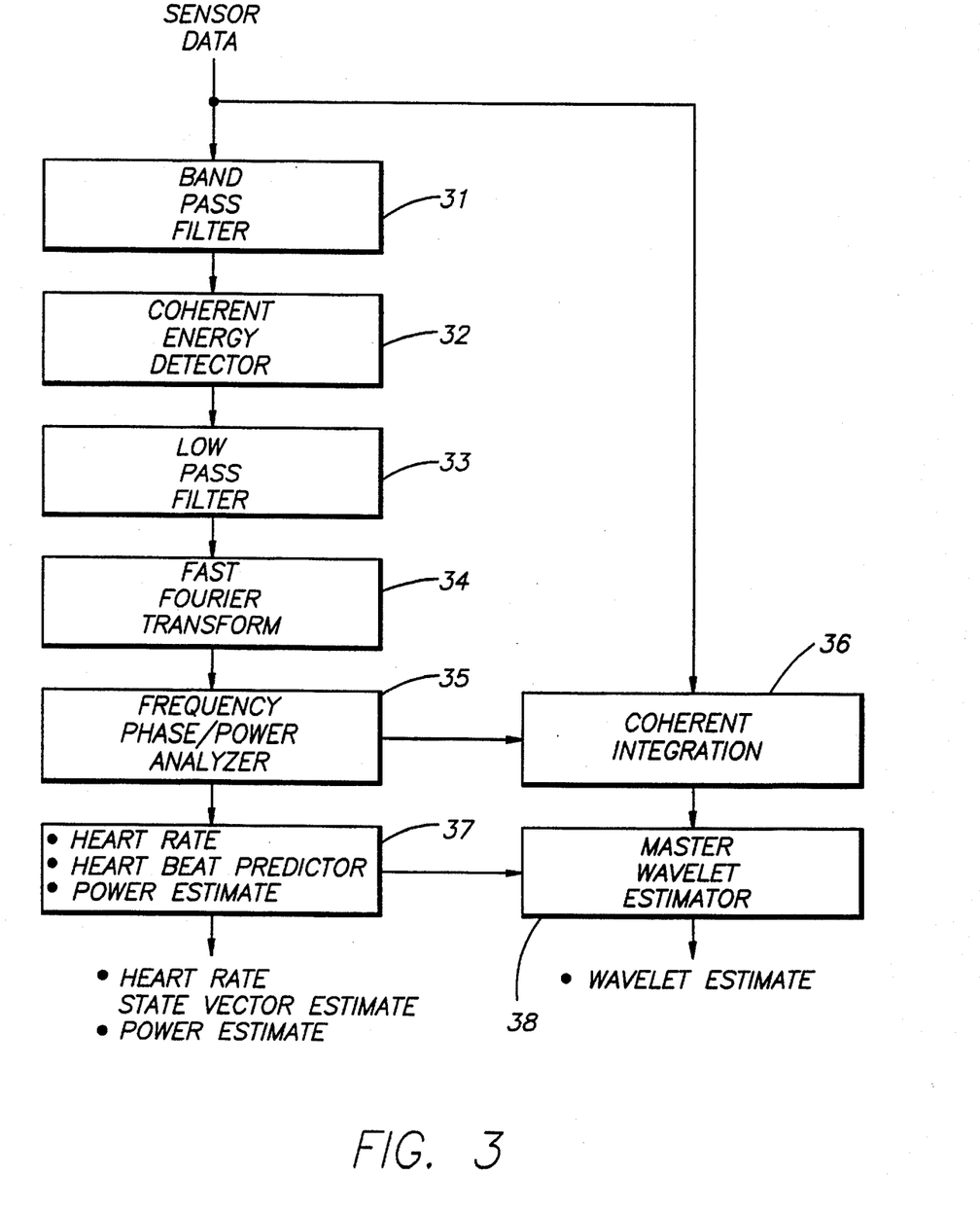
FIG. 3 is a flow diagram showing the flow of information for the initialization algorithm used in the invention shown in FIG. 2.

FIG. 3 shows the main functional elements of the initialization algorithm carried out in block 22 in FIG. 2. The sensor data is subjected to band pass filtering in block 31 to improve the signal to noise ratio and eliminate aliasing. That is, errors which may be introduced in subsequent operations which include a fast Fourier transform. The output signal from block 31 is coherently detected in block 32 through the use of an energy detector, a bank of potential wavelet basis functions. Block 33 provides low pass filtering of the output of block 32 along with decimating the signal at a sample rate of typically 10 Hz. The sampling in block 32 results in a sequence of peaks at a periodic interval corresponding to a 5 second sequence of initial detections. Block 33 is coupled to block 34 where a zero filled Fourier transform is used to detect the period and location of the peaks from the phase. Blocks 35–38 analyze the signal from block 34 to provide the starting parameters for the processor algorithm. If the vital sign being monitored is the heart beat, then the location in time and the rate of the heart beat are used to focus the windowing function. The detected image of the heart beat wavelet is focussed in block 36 by coherently averaging the 5 seconds of data used in the initialization processing. The processor also extracts the typical power levels of the signal of interest while minimizing the noise background in blocks 37 and 38.

Figure 4:
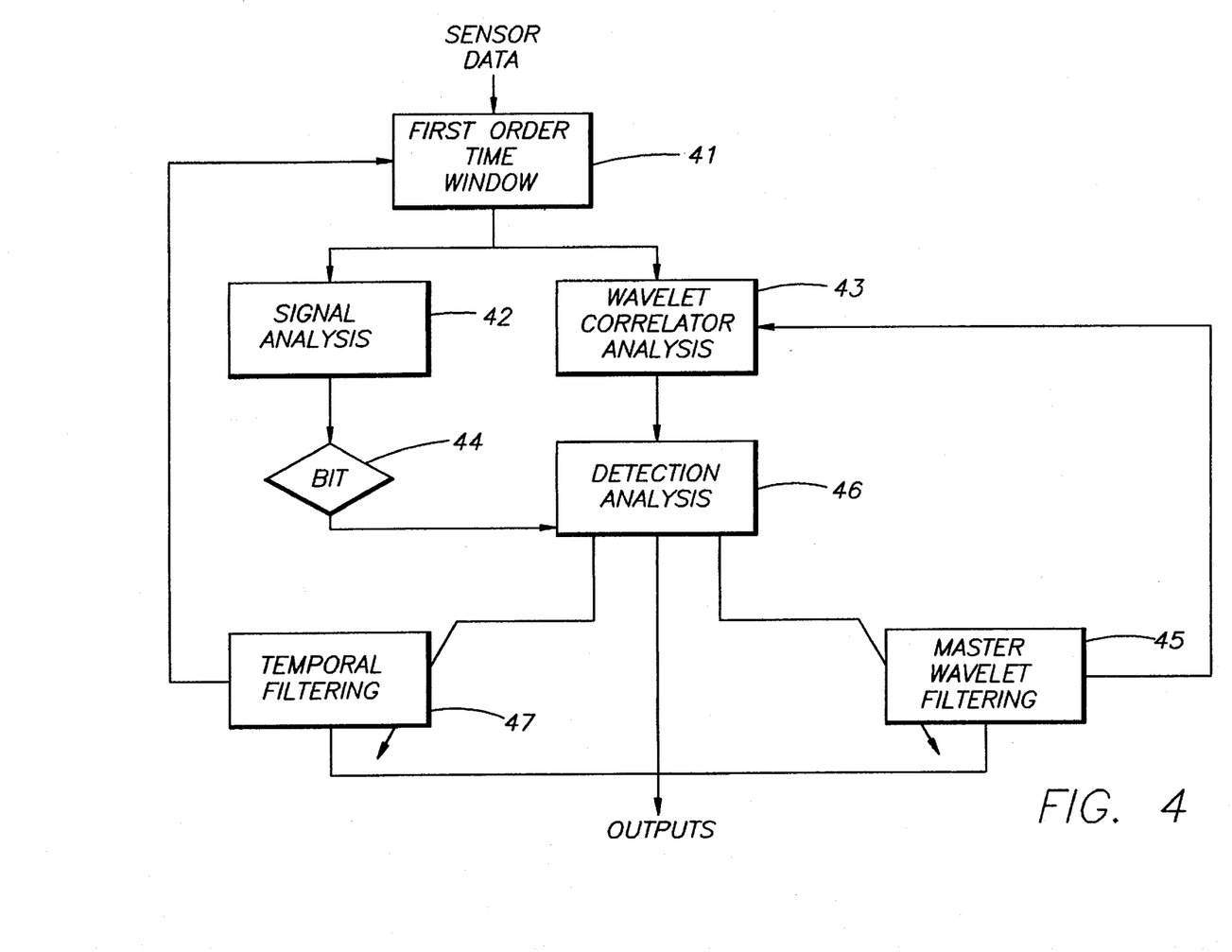
FIG. 4 is a flow diagram showing the main processor flow of information in carrying out the invention shown in FIG. 1.

FIG. 4 shows the flow of information in the main processor during the steady state operation of the invention. Sensor data is introduced into block 41 which provides a first order time window based on the initialization. Block 41 is coupled to blocks 42 and 43. Block 42 carries out processing to determine if there is a "flat line" condition, or excessive interference, or if detection is even possible. Block 42 is coupled to block 44 which carries out a built in test (BIT). Actually, part of the test is performed in block 42. The BIT is performed continuously and instructs the algorithm to repeat, continue to its next stage, or signal the attendant. During monitoring, however, the input signals are formatted and transmitted as required and various interrupts are serviced.

Block 43 is a coherent matched filtering performed in real time on the conditioned input data using the range of wavelets from the master wavelets filtering from block 45. Block 46 peak detects the signal from block 43. The peak signal is evaluated after normalization. The peak signal is used to extract information to update the temporal filtering in block 47 adaptively to estimate the event location and rate update. The peak signal is also used to update the master wavelet filtering adaptively to estimate the master wavelet spectral content and time image. Any or all of the information in block 45 and block 47 can be selectively outputted to the user. The gain and feedback loops should be selected to maintain the proper balance between estimators and output event declarations.

Figure 5:
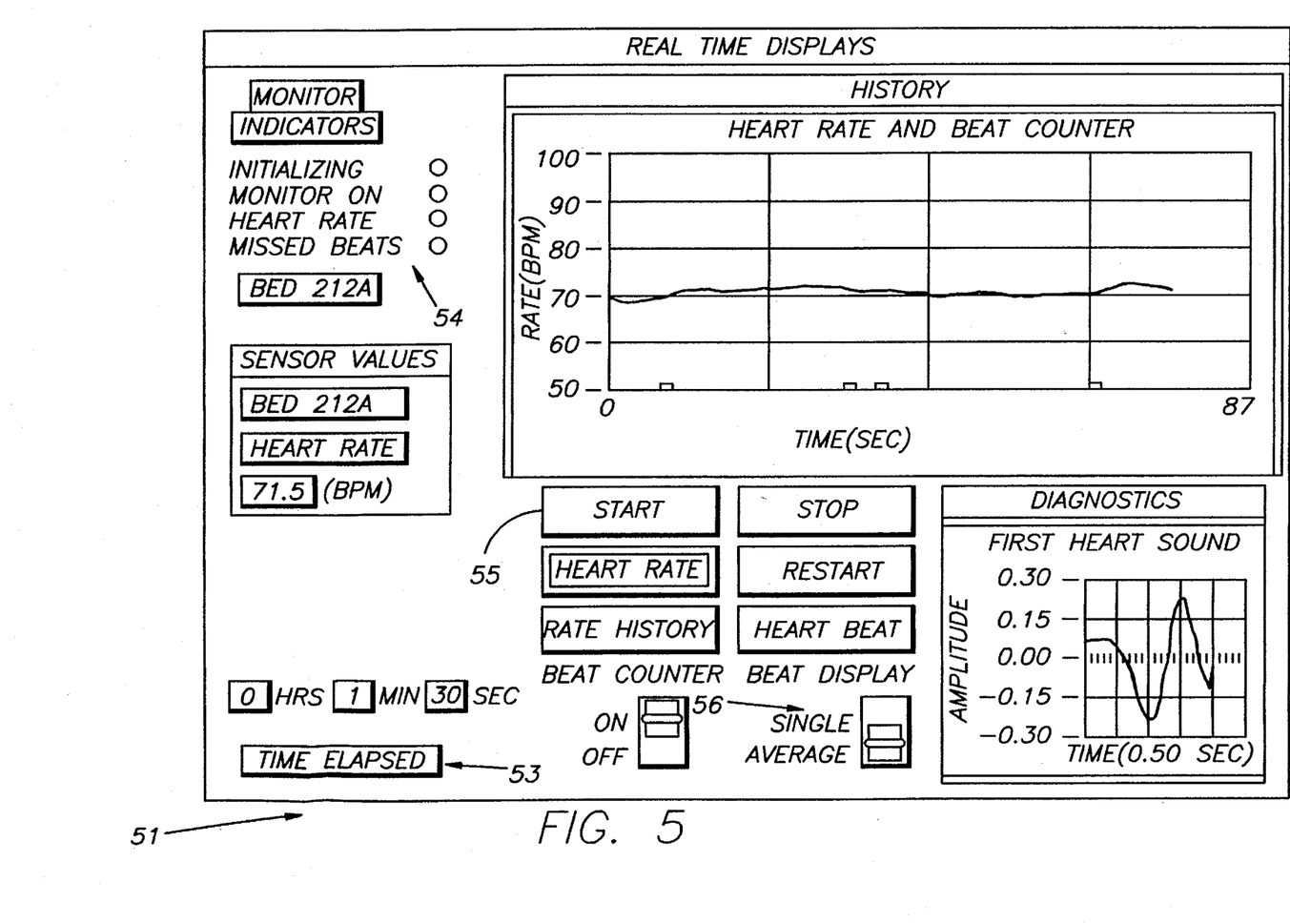
FIG. 5 shows a front view of a typical operating system display set incorporating the invention.

FIG. 5 shows the front panel 51 of experimental equipment based on one embodiment of the invention for monitoring a person's heart. The lower center of the panel 51 contains switches and buttons for controlling the operation and displays. The lower left has an elapsed time clock 53 and the upper left has status signal lights 54 for alerting the medical attendant.

At the start of monitoring, start 55 is depressed and after about 5 seconds, the initialization light turns off and the monitor "on" light goes on. The monitor light remains on until either the stop or restart buttons are depressed, or if the BIT in FIG. 4 is failed. Heart rate deviations are evident by the heart rate light and the lack of detected heart beats is evident by the missed beat light. The light "on" conditions are accompanied by audio alarms. These responses are programmable and depend on the quality of the filter states and the BIT as well as preset conditions determined by the operator.

The area on the left labeled as "SENSOR VALUES" allows the invention to be used to read instantaneous physiological vital signs either at the location of the instrument or remotely through telephone lines, or hard wiring, or a transmission. The upper right portion entitled 'HISTORY" can be selectively displayed to show the latest 100 seconds of the heart beat at a 1 second rate. This display can be selected to be a selected previous time such as the previous 4 hours. Another possible display is the missed beat activity. Appropriate programming allows a wide range of possible displays depending on the desired information.

The lower right hand portion of the panel 51 labeled "DIAGNOSTICS" can show the first heart beats as averaged over the last 2 minutes, or if the beat display 56 is selected to be "single", the real time beats are shown. The display can be altered to show the time or the spectral representation and used to aid a physician to diagnose ailments in a manner similar to the use of the EKG electrical signal.

Detailed Description

Figure 6:
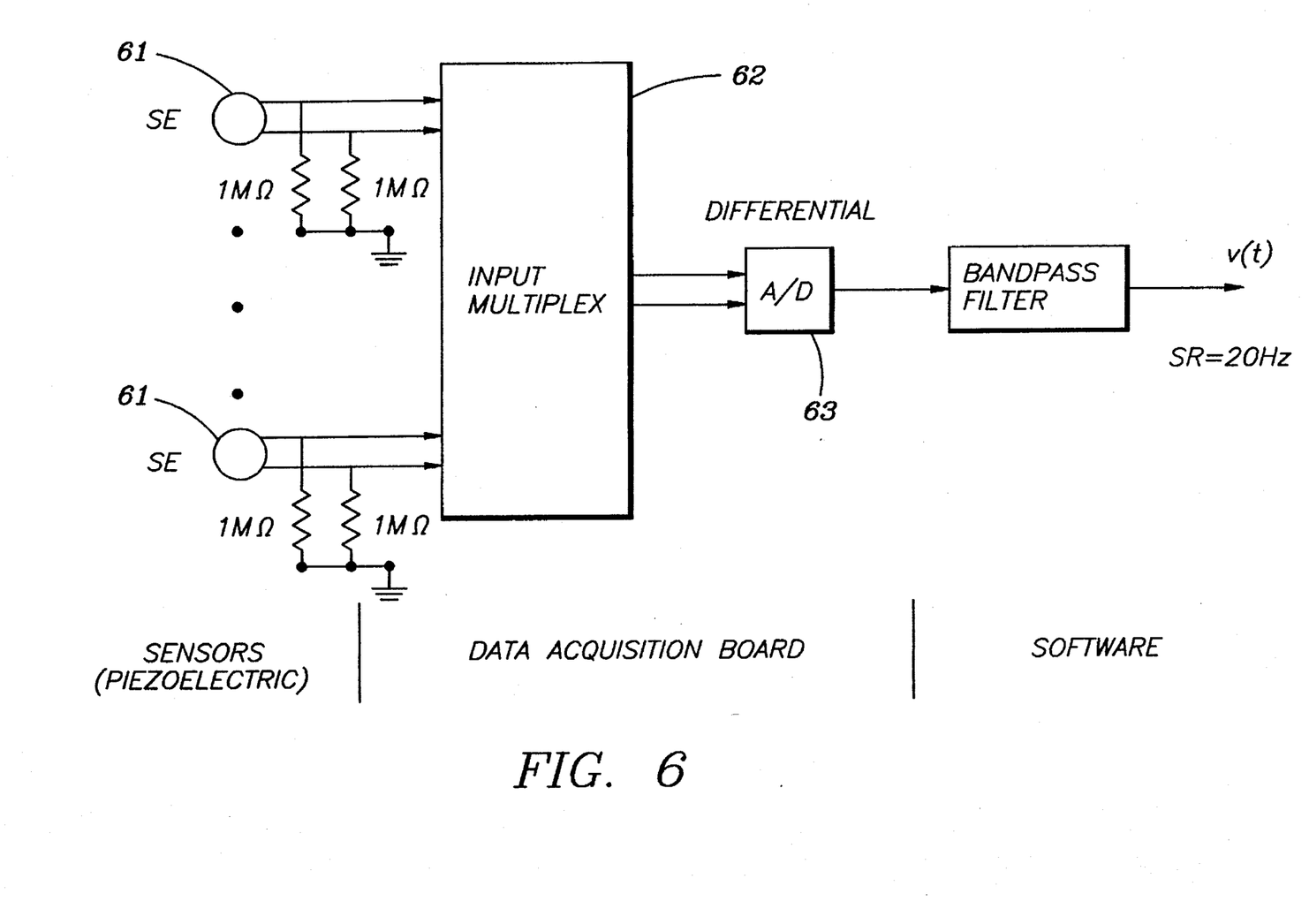
FIG. 6 is a block diagram showing the collection of sensing data used in the invention as shown in FIG. 1.

FIGS. 6–9 show more detail of preferred embodiments of the invention. FIG. 6 is a block diagram of the arrangement of the collection of data. A plurality of sensors 61 such as eight separate sensors are coupled to a multiplexer unit 62 and are grounded through 1 megohm resistors as shown. The typical sample rate of the multiplexer unit 62 is 20 Hz.

It is convenient to use a laptop computer (not shown) for carrying out data processing. The multiplexer unit 62 is coupled to a differential analog to digital converter 63. The differential analog to digital converter 63 can be implemented using a software controlled DAQCARD-700 available from National Instruments Corporation. The DAQCARD-700 allows up to 8 analog input signals for differential analog to digital conversion which is digitized by time multiplexing to a single output signal.

Figure 7:
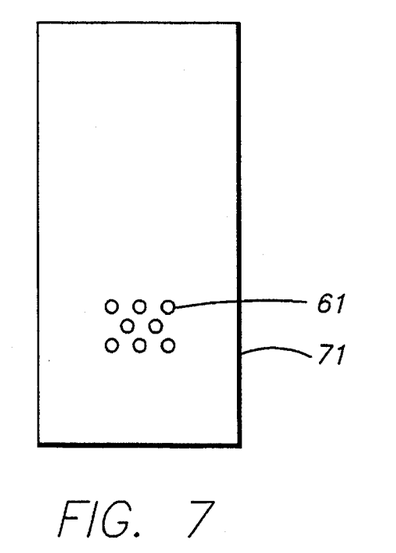
FIG. 7 is a top sectional view of a mattress showing embedded sensors for carrying out the invention according to FIG. 1.
Figure 8:
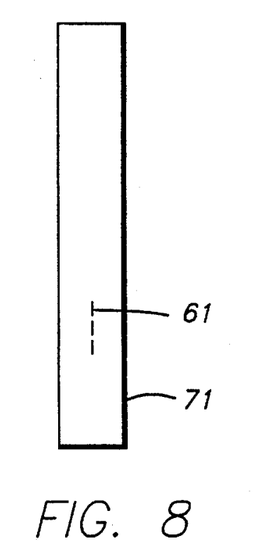
FIG. 8 is a side elevational sectional view of the mattress shown in FIG. 6.

FIGS. 7 and 8 show a typical arrangement of the sensors 61 in a foam mattress. In FIG. 7, the top row of the sensors 61 is spaced about 4 inches from the bottom row and each of the sensors 61 in the middle row is spaced about 2 inches from the nearest sensor 61 in the top and bottom rows.

The DAQCARD-700 digitizes each input channel in sequence and produce an average signal as follows:

$$v(t)=1/N\Sigma v_i(t_i)$$

as each voltage is sampled at 20 Hz, the effective sampling rate is 160 Hz. The processing is performed using standard double buffering in which a block of data is digitized while a prior block of data is being processed. Any spatially out of phase signals to the sensors 61 are suppress through the processing. The real time averaging in the differential analog to digital converter 63 is effectively a low pass filter.

For the parameters being used, namely a sampling rate of 20 Hz and N=8, the attenuation of the amplitude at the frequency of interest, 5 Hz, is about 10% and the half power (3 db) is at about 8 Hz. The bandwidth can be modified by averaging with weighted coefficients to create an effective band pass filter, rather than a low pass filter. It is also possible to increase the sample rate and then decimate to effect a bandwidth change.

Utilizing the invention to detect heart beats requires consideration of the expected characteristics of the signals generated by heart beats. Heart beat detected in a bed primarily through the upper body cavity are characterized by having most of the energy centered in the frequency range of 20 Hz to 30 Hz. Generally, the frequency width is about 10 Hz and it can have a center frequency as low as 15 Hz or as high as 45 Hz. Accordingly, the system parameters include the sampling rate, low pass filter, etc. must be scaled to suit the physiological vital signs being measured. The typical sampling rate is in the range of 150 Hz to 200 Hz range. In stead of the low pass filter operation described above, a sampling rate of as high as high as 320 Hz can be used followed by a fast fourier transform (FFT) which is decimated to a sampling rate of 40 Hz. The FFT acts as a bank of band pass filters and the resulting complex time series has an improved signal to noise ratio at a lower sampling rate.

Figure 9A:
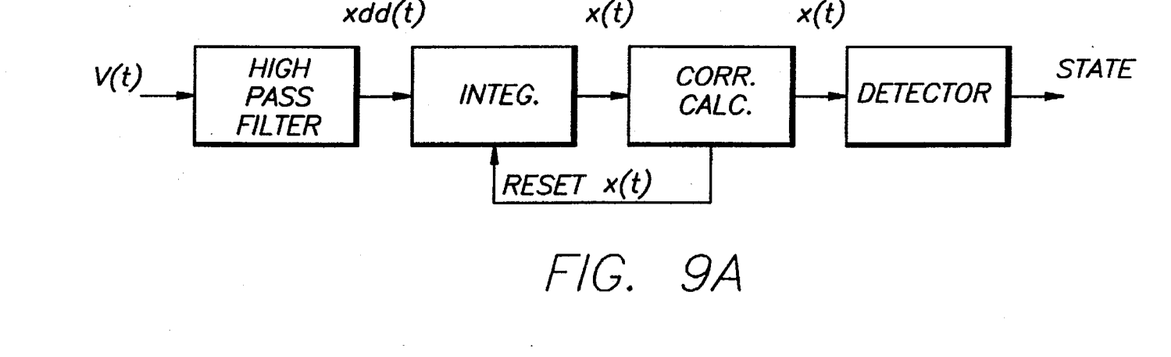
FIGS. 9a and 9b show the block diagram and flow diagram, respectively, of the patient presence determination system according to the invention.
Figure 9B:
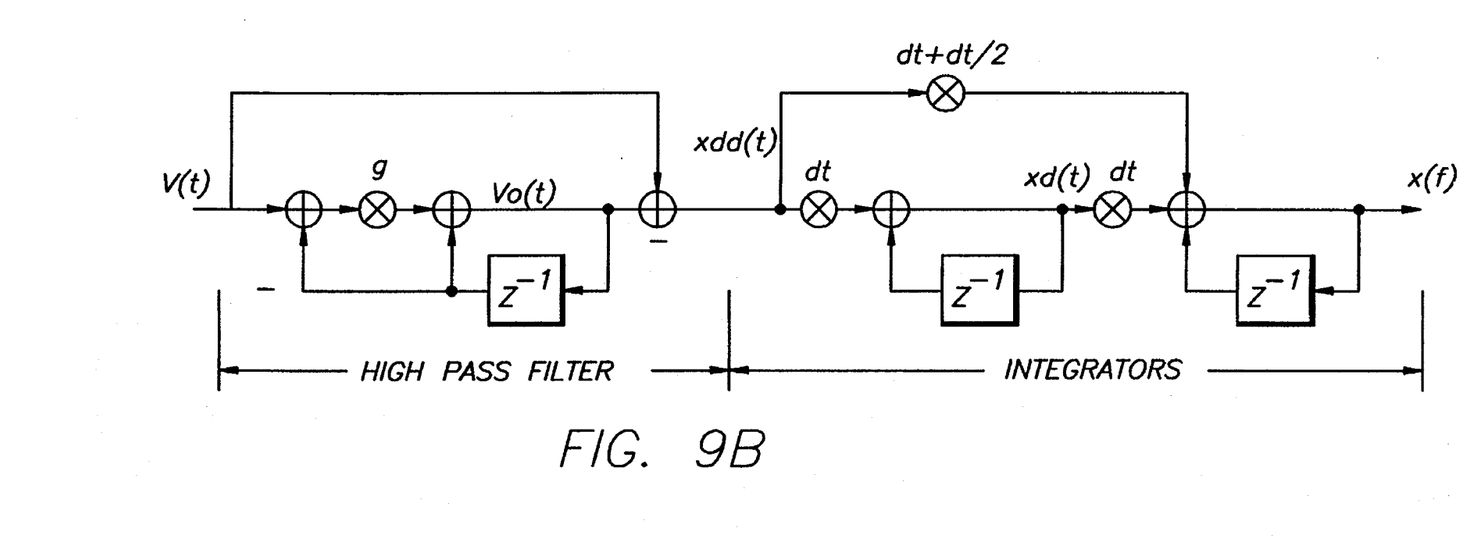

FIGS. 9a and 9b show an overall block diagram and corresponding detailed flow diagram, respectively. One important algorithm is to determine whether or not a patient is present. The (occupied) algorithm makes this determination and can have the filters in the system "coast" or predict ahead to enable a suitable re-start when the patient returns. For this algorithm, the sensors being used measure acceleration, have a long time constant, and low level, high frequency noise. As these are inexpensive sensors compensations in the processing are made to compensate for the deficiencies of these sensors. When the initialization algorithm is started, it is assumed that the chair or bed is occupied by a patient. If desired, the start of the algorithm can be made even if the bed or chair is unoccupied. In FIG. 9b, the symbol "$z^{-1}$" is the conventional symbol for a lag-1 (dt) operator in digital signal processing analysis (z-transforms). Generally, the corresponding portions in FIGS. 9a and 9b relating to the high pass filter and integrators is indicated. The basic equation corresponding to the high pass filter is as follows:

$$g=0.999$$

$$vo(t)=vo(t-dt)+g*[v(t)-vo(t-dt)]$$

$$xdd(t)=v(t)-vo(t)$$

The "g" term is a time constant determined by calculation to minimize the response to unwanted low frequencies associated with the heart and breathing. The term "dt" corresponds to the sample interval. The term "xdd(t)" is the detected acceleration of the cushion or bed. The term "xd(t)" is the rate and "x(t)" is the flex of the sensor.

The integrators can be represented as follows:

$$xd(t)=xd(t-dt)+xdd(t)*dt$$

$$x(t)=x(t-dt)+xd(t)*dt+xdd(t)*dt*dt/2$$

where xd(o)=0 vo(0)=0 x(o)=0.0008 dt=1/20 sec.

The correction calculation resets the threshold.
Correction to reset x(t)

ed=0.00001 e=0.0005 (for the detector)

If [(xd<ed) and (xdd<ed)]
then {if (x<e),then x=0}

The decision is made in the detector through a comparator.

Detector Logic $e = 0.0005$

If($x > e$)     state = sitting or else     state = not sitting.

Equations corresponding to the flow diagram shown in FIG. 3 for the Initialization follow:

For a high signal to noise (SNR>3 dB), the first three blocks 31, 32 33 can be replaced with an energy (or variance) detector (where t=n*dt is replaced by n):

$$pow_{Lo} = (1/L)* \sum_{n=L_o+1}^{L_o+L} (v(n)-\bar{v}_o)*(v(n)-\bar{v}_o)$$

where $$\bar{v}_o=(1/L)*\Sigma v(n)$$

L=the length of a 'filter', wavelet, or heart beat, typically 8–10 points for the embodiment (with sample rate 20 Hz) and n refers to the time sample index.
Therefore $$pow_{Lo} = (1/L)* \sum_{n=L_o+1}^{L_o+L} (v(n)-\bar{v}_o)*v(n)$$

$$pow_{Lo} = \sum_{n=1}^{L} w_n * v(n = L_o)$$

where $$w = (1/L) * [v(n+L_o) - v_o]$$

or w=matched filter or wavelet function the function $\overline{pow}$ which corresponds to the variance or power is sampled at 10 Hz over all potential wavelets over the first 5 seconds of data (i.e. 50 points per wavelet). The subscript for the wavelets will be suppressed for convenience. The best match for period and wavelet is found.

The following variables are computed for later use:

max=the maximum value squared of $\overline{pow}$ $$cn = L * \sum_{n=1}^{L} w_n^2$$

$$c1 = (cn * cn)/L * L$$

The following is an example of an implementation:

After zero filling to 512 points and DC (mean) removal, an FFT is computed and the peak amplitude located at 'loc' corresponding to a potential heart beat frequency of 40 bpm–90 bpm. Zero filling is a standard technique in FFT processing to evaluate the spectrum at additional frequency values, basically interpolating, between the normal values.
Then $$sigavg = \sqrt{[max/cn]} \quad \text{nominal power level}$$

$\alpha = [max/c1]$ $\overline{w_n} = \sqrt{\alpha}\, w_n$ normalized nominal master wavelet
$W(f) =$ Fourier Transform of $w_n$
$dtau = 51.2 * SR/loc$    heart rate period estimate in points per beat (each point is $dt$ sec)

If $[\phi(loc) > 0]$    spot $= (1 - \phi/2\pi) * dtau$
or else    spot $= (0 - \phi/2\pi) * dtau$ where $\phi$ (loc) is the phase of the FFT at loc (corresponding to the phase of the heart beat location), and spot is the time (pointer value) of the first heart beat.

Using spot and dtau, the time of the next heart beat (after the first 5 seconds) is estimated (tau). Also, if the energy detection is used instead of wavelet basis functions, then the master wavelet can be computed via coherent stacking over the initial 5 seconds of all heart beats, taking care of the time weighted normalization required.

The algorithm uses pointers for the state vector tau and dtau where tau is the time array pointer and dtau is the number of points between beats. (For a typical embodiment, 1 second is 20 points.)

As to FIG. 4 which involves a real time processor algorithm, the following equations are relevant.

From the set-up and initialization:

$$Y = \begin{pmatrix} tau \\ dtau \end{pmatrix} \text{ is the state vector}$$

tau is the time location of the heart beat $$P = \begin{pmatrix} 7.5 & 0.0 \\ 0.0 & 0.25 \end{pmatrix} \text{ is the state vector covariance}$$

$R = R0 = 1.5$ is the measurement covariance $$H = \begin{pmatrix} 1 \\ 0 \end{pmatrix}$$

$$\Phi = \begin{pmatrix} 1 & 1 \\ 0 & 1 \end{pmatrix} \text{ is the time transition matrix}$$

$$Q = \begin{pmatrix} 0.75 & 0.0025 \\ 0.0025 & 0.0025 \end{pmatrix} \text{ is the stochastic matrix}$$

The variables and notations used herein follow the definitions and conventions of any standard text on Kalman Filtering such as Brown, R. G., *Introduction to Random Signal Analysis and Kalman filtering*, John Wiley and Sons, 1983. The values are the result of system and performance modeling as per the text and standard practice.

Figure 10:
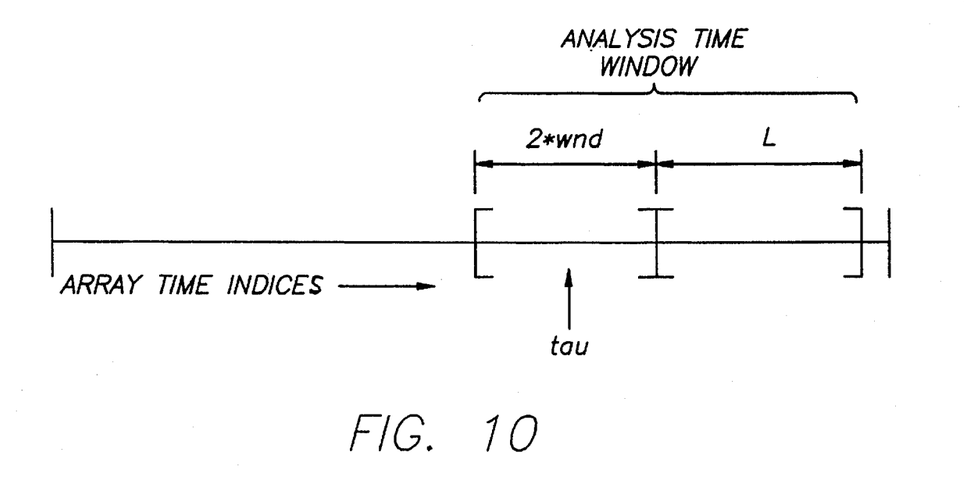
FIG. 10 shows a time display for defining a parameter of the invention.

The 'window' parameter is defined in connection with FIG. 10 as $$wnd = [P(O) = R]^{1/2} * 4$$

and the data to be analyzed is (First Order Time Window)

$$N = L + 2 * wnd$$

points in length 'centered' on tau are shown in FIG. 10.

This window is real time adaptive in length and location though it is never longer than the initial window as shown below.
Let $$dat(n) = v(n')$$

where the N points are selected via the window function.

Signal Analysis Function $$sigdat = \left[ (1/N) * \sum_{n=1}^{N} [dat(n) - \overline{dat}] \right]^{1/2}$$

where $$\overline{dat} = (1/N) * \sum_{n=1}^{N} dat(n)$$

The following is an analysis of a narrow 'power' window.
For the a typical embodiment, if sigdat is 6 dB below nominal, (sigavg) is then the status is defined as
'no activity'
if sigdat is 6 dB above nominal, (sigavg) is then the status is defined as
'excessive activity'
if sigdat is within 6 dB of nominal then Wavelet Correlator Analysis is computed via a frequency domain equivalent of:

$$C(\hat{\tau}) = \frac{1}{\sqrt{L * N}} * \frac{\sum_{n=1}^{N} [dat(\hat{\tau} + n) * w_n]}{\left\{ \frac{1}{N} \sum_{n=1}^{N} [dat(n)]^2 * \frac{1}{L} \sum_{n=1}^{L} W_n^2 \right\}^{1/2}}$$

The correlator array is searched for a peak of amplitude (max) at location (loc) where loc is within

*tau+/−wnd*

If max>0.125, then z=loc (with the proper care of pointer indices.

The search for the peak is over the set of wavelet functions in the neighborhood of the nominal (master)wavelet.

Temporal Filtering Update (via a Kalman-like Filter)

$eps = z - tau$     (properly normalize pointers)
if max < 0.125     $R = 60$
$0.125 < max < 0.2$     $R = 60 - 59*max/0.2$
$0.2 < max$     $R = 1 - 0.25*(max - 0.2)/0.8$ then $$K=P*H^T/(H*P*H^T+R)$$

$$Y+Y+K*eps$$

$$P=(I-K*H)*P$$

$$Y=\Phi*Y$$

$$P=\Phi*P*\Phi^T+Q$$

and $$wnd=4*[P(O)+R]^{1/2}$$

The maximum wnd allowed is initial wnd.

Master Wavelet Filtering if max>0.125 then let $$w=\{dat_{LOC}, dat_{LOC+1}, \ldots, dat_{LOC+L-1}\}$$

$$\overline{w} = (1/L)* \sum_{n=1}^{L} w_n$$

$$G=(0.05-0.01)*(max-0.125)/(1.0-0.125)+0.01$$

$$W_n=W'_n+G*(\hat{w}_n\overline{w}-w'_n)$$

is the update filter and w' refers to the previous values.
The spectrum is computed for use in the correlator block.
The following are additional system parameters relative to FIG. 5 with respect to the displays and alarms.
In an operating embodiment, the display is updated each second and incorporated in the Toshiba Laptop (Model T1910 series). (See below)

Most of the alarms are triggered via a running average of an 'M out of N' counter of the form $$ctr(t)=ctr(t-dt)+g* \{value\ (t)-ctr(t-dt)\}$$

where a typical g is 0.1 and thresholds are 0.6–0.9.

'agitated' patient—uses the excessive power variable from the signal analysis

'heart beat' missed—value is 1 if low power or adequate power and low correlation.

heart rate—alert requirements can be set by the operator as upper and lower bounds or a band around the nominal from the initialization or over some nominal time history.

Display of the heart beat—can be averaged=wavelet ($w_n$) or single=real time data array ($dat_n$)

Receiver/Alerts to the Attendant

The implemented embodiment uses simulated LED's and audio signals.

The implementation can use any wired or wireless, telephone, pager, etc. system.

A preferred implementation is to interface this smart sensor system to an existing emergency call system.

A valuable option is to store the history internally and down load via a modem or hard wired connection to a main work station or hand carried nurse's logging device or recorder.

There has been described a novel non-invasive medical monitor system. It is evident that those skilled in the art may now make numerous uses and modifications of and departures from the specific embodiments described herein without departing from the inventive concepts. Consequently, the invention is to be construed as embracing each and every feature and novel combination of features present or possessed by the accessory herein disclosed and limited solely by the spirit and scope of the appended claims.

I claim:

1. An apparatus operable for monitoring physiological vital signs of a human body as indicated by a movement and/or acoustical wave produced by the body without physically contacting the body; said apparatus comprising sensing means operable to transform a movement and/or acoustical wave produced by said body into an electrical signal; signal processing means coupled to said sensing means and operable to receive said electrical signal from said sensing means and to process said electrical signal adaptively using wavelet correlator analysis; said signal processing means having an output signal indicative of the movement and/or acoustical wave producing said electrical signal.

2. The apparatus as claimed in claim 1, further comprising display means and coupling means operable for coupling said display means to said signal processing means; said display means operable for displaying said output signal in a form representative of the physiological vital sign being sensed from the movement and/or acoustical wave of the body generating said electrical signal.

3. The apparatus as claimed in claim 2, wherein said coupling means is a direct electrical connection.

4. The apparatus as claimed in claim 2, wherein said coupling means comprises transmitting means operable for establishing a coupling though an electromagnetic transmission.

5. The apparatus as claimed in claim 1, wherein said signal processing means comprises means for selectively processing data for preselected physiological vital signs.

6. The apparatus as claimed in claim 1, wherein said signal processing means is operable for being initialized for a body by utilizing said electrical signal to establish matched filters corresponding to preselected physiological vital signs.

7. The apparatus as claimed in claim 1, wherein said signal processing means comprises an initialization means operable for initializing said apparatus for a body; said initialization means comprising bandpass filter means operable for selectively band passing signals within a predetermined frequency band; coherent energy detector means operable for coherently detecting a predetermined signal; lowpass filter means operable for selectively passing signals less than a predetermined frequency; fast Fourier transform means operable for producing a fast Fourier transform of an input signal; and analyzing means operable for determining the starting parameters for said signal processing means; said analyzing means comprising in combination a frequency phase/power analyzer; coherent integrator; and signal estimating means operable for estimating physiological vital sign parameters and a master wavelet.

8. The apparatus as claimed in claim 1, wherein said signal processing means establishes data flow in which said electrical signal is used to establish a first signal corresponding to a first order time window; said first signal is used for producing a second signal from a signal analyzer and a third signal from a wavelet correlator; said second signal is used in a built in test of the system to produce a fourth signal; said third and fourth signals are used to establish that a suitable signal is present in said electrical signal and to produce a fifth signal; said fifth signal is used to modify a temporal filter, and a master wavelet filter, which are coupled together, and an output signal; said temporal filter being coupled to receive said first signal and said master wavelet filter being coupled to said wavelet correlator.

* * * * *